United States Patent [19]

Coia et al.

[11] Patent Number: 4,971,798
[45] Date of Patent: Nov. 20, 1990

[54] HARD CONFECTIONS CONTAINING HYDROGENATED ISOMALTULOSE AND MEDICINALLY ACTIVE INGREDIENT

[75] Inventors: Kenneth A. Coia, Elkhart, Ind.; Michael J. Lynch, Bridgewater, N.J.

[73] Assignee: Miles Inc., Elkhart, Ind.

[21] Appl. No.: 443,182

[22] Filed: Nov. 30, 1989

[51] Int. Cl.$^5$ ............................ A61K 9/20; A61K 9/22
[52] U.S. Cl. ....................................... 424/440; 514/777; 514/849; 514/850; 514/853; 514/948
[58] Field of Search ........................................ 424/440

[56] References Cited

U.S. PATENT DOCUMENTS

| 3,427,379 | 2/1969 | Barry et al. | 424/440 |
| 4,117,173 | 9/1978 | Schiweck et al. | 426/548 |
| 4,139,627 | 2/1979 | Lane et al. | 424/440 |
| 4,233,439 | 11/1980 | Schiweck et al. | 536/4 |
| 4,323,588 | 4/1982 | Vink et al. | 426/564 |
| 4,372,942 | 2/1983 | Cimiluca | 424/440 |
| 4,551,329 | 11/1985 | Harris et al. | 424/440 |
| 4,572,916 | 2/1986 | Lindley | 514/777 |
| 4,587,119 | 5/1986 | Bucke et al. | 424/48 |
| 4,714,620 | 12/1987 | Bunick et al. | 426/572 |
| 4,788,145 | 11/1988 | Munir | 435/100 |
| 4,792,453 | 12/1988 | Reed et al. | 426/5 |
| 4,810,516 | 3/1989 | Kung-Caan | 426/548 |
| 4,840,797 | 6/1989 | Boursier | 424/475 |
| 4,911,937 | 3/1990 | Crosello et al. | 426/660 |
| 4,921,939 | 5/1990 | Nofre et al. | 426/548 |

FOREIGN PATENT DOCUMENTS

303295A2 2/1989 European Pat. Off. .
WO88/06449 9/1988 PCT Int'l Appl. .

OTHER PUBLICATIONS

Corbiere Chem. Abstr. 110(8):63766q (1988) of PCT/WO 88 06449 Sep. 7, 1988.

*Primary Examiner*—Shep K. Rose
*Attorney, Agent, or Firm*—Jerome L. Jeffers

[57] ABSTRACT

Disclosed is a hard confection containing Palatinit (hydrogenated isomaltulose) and a medicinally active ingredient. Such a formulation has been found to dissolve more slowly than similar formulations based on sugar rendering them suitable for dispensing the active ingredient over an extended period of time.

10 Claims, No Drawings

HARD CONFECTIONS CONTAINING HYDROGENATED ISOMALTULOSE AND MEDICINALLY ACTIVE INGREDIENT

BACKGROUND OF THE INVENTION

Hydrogenated isomaltulose sold under the tradename Palatinit ® by the Palatinit GmbH of Mannheim, Germany, also known as isomalt, is a sugar substitute which can be used in place of sucrose, glucose or similar sugars for the production of foodstuffs. This material may be classified as a carbohydrate, more specifically, as a hydrogenated disaccharide. The production of hydrogenated isomaltulose involves an enzymatic rearrangement of saccharose into a more stable compound known as isomaltulose (tradename Palatinose). Following a purifying crystallization, the isomaltulose is hydrogenated to form the resulting Palatinit which is described as an odorless, white, crystalline, nonhygroscopic substance containing about 5 percent water of crystallization. This material contains approximately 2.1 calories/gm and has a sweetness of about half that of sucrose. The reduced caloric value results from the fact that Palatinit is only partially metabolized, so that its caloric utilization is only 2.1 calorie per gram.

In U.S. Pat. No. 4,792,453 there is disclosed a hard coated chewing gum comprising a sugarless chewing gum center having a hard coating comprising hydrogenated isomaltulose preferably in an amount of from 50 to 75 weight percent of the coating.

There is disclosed in U.S. Pat. No. 4,840,797 a confectionary or pharmaceutical product having a hard, sugarless coating, comprising xylitol, mannitol or maltitol. Sorbitol is also mentioned in this regard.

Published European Patent Application 0 303 295 $A_2$ describes a hard candy comprising meso-erythritol as the main component together with other saccharides such as sucrose, glucose, thick malt syrup, fructose, and isomerized sugars as well as palatinose and isomaltose.

U.S. Pat. No. 4,587,119 discloses the use of isomaltulose as a total or partial substitute for sucrose in the preparation of food and pharmaceutical products for human or animal consumption. This patent mentions orally-administered ingested pharmaceutical compositions as well as those which are taken into the mouth but not with the intent of being ingested such as toothpastes, tooth powders, mouth washes, gargles, dental lotions and chewing gums.

SUMMARY OF THE INVENTION

The present invention is a hydrogenated isomaltulose based hard confection which contains, in addition to the hydrogenated isomaltulose, a medicinally active ingredient.

DESCRIPTION OF THE INVENTION

The term hard confections refers to amorphous products prepared by evaporation of water from a sugar solution so as to concentrate it to a solid content of not less than 95% by weight. The present invention involves replacing the sugar with Palatinit, i.e. hydrogenated isomaltulose, and incorporating therein an active ingredient to produce solid confections containing one or more active, medicinal ingredient.

Presently, the preferred method of manufacturing hard confections involves cooking sugar solutions in a kettle under constant slow agitation until the solution starts to boil. Agitation is discontinued and the pressure is dropped to 22-25 inches of Hg whereupon the mix is held under this slight vacuum for a period of from 3-10 minutes. Typically, the sugar mix is heated to 266°-320° F., preferably 280°-310° F. Acids, color and/or flavorings are added and the mix is either molded or stamped into various shapes and sizes. As compared to what might be expected based on the manufacture of sugar hard confections, Palatinit containing hard confections require higher temperatures of 300-330° F. for manufacturing. Palatinit is suitable for use in hard confections because of its sweet taste and contributes low caloric content. The discovery that Palatinit based confections dissolve more slowly than those containing sugar renders this material particularly suitable for use in a hard confection containing an active, medicinal ingredient due to the longer duration of medicinal activity that can be achieved thereby.

Typically, medicinal agents that can be added to the Palatinit based hard confection are antitussives, e.g. dextromethorphan hydrobromide as well as decongestants, antihistamines and/or expectorants.

More particularly, if it is desired to treat a sore throat, cough and nasal congestion one could combine hexylresorcinol (2.4 mg) and menthol (10 mg) in a unit dosage form of the hard confection. When nasal congestion is the problem, phenylpropanolamine hydrochloride (25 mg) may be added or in the case of a mild sore throat hexylresorcinol (2.4 mg) or dyclonine hydrochloride would be indicated. When suppression of a cough combined with a sore throat is indicated one could use a combination of dextromethorphan hydrobromide (5.0 mg), menthol (5.0 mg), menthol eucalyptus (5.0 mg), benzocaine (5.0 mg) and cetylpyridinium (1.66 mg) where menthol and eucalyptus serve the dual function of medicament and flavoring agent.

A typical formulation will contain, on a w/w basis, 50 to 98% Palatinit and from 1.0 to 15 mg per dosage of the active ingredient. The confection will normally contain other ingredients such as flavoring agents; e.g. oils derived from plants and fruits such as citrus oils and fruit essences; artificial sweeteners to enhance the sweetening power of Palatinit; e.g. Aspartame, Acesulfame-K, and saccharin, flavoring agents; e.g. natural or synthetic flavors and/or oils derived from plants, leaves, flowers and fruits such as lemon, honey, cherry, menthol, eucalyptus, peppermint and spearmint; natural or synthetic coloring agents and perhaps a binding agent selected from the group of alginate, cellulosic, vegetable gums and the like.

Flavoring agents contemplated for use in the present invention may be added to the hot syrup in an amount such that the finished confection will contain from about 0.05 to 0.3 weight percent and preferably 0.1 to 0.2 weight percent of the flavoring material. Artificial sweeteners, when used, are typically added to the syrup in sufficient amount to provide the desired sweetness in the finished products. The amounts used will depend on the sweetening power of the particular artificial sweetener selected and will typically range from 0.05 to 0.25 weight percent of the finished formulation. Coloring agents are typically food quality dyes or lake added directly to the syrup in the dye form. Exemplary of such dyes are Blue #1 or #2, Red #3 plus #40, Yellow #5 or #6, titanium dioxide or blends of these dyes selected to produce the desired color. Alternatively, natural colors such as carmine, annatto, beta carotene, turmeric, beet, grape skin extract, caramel, and blends thereof may be used as the colorant. Typical use levels for the coloring agent range from 0.01 to 0.03% for synthetic dyes with levels of from 0.1 to 1.0% for the natural colorants. In addition, organic acids are typically added to the formulation for the purpose of providing tartness. Suitable acids include citric, malic, maleic, fumaric, succinic, adipic and tartaric acid.

A typical formulation will contain:

| Ingredient | Wt % | Preferred % |
|---|---|---|
| Palatinit | 10.0–99.0 | 50–98 |
| Acid | 0.1–5.0 | 0.2–2.5 |
| Flavor | 0.01–2.5 | 0.05–0.3 |
| Color | 0.01–2.0 | 0.05–1.5 |
| Sweetener | 0.05–0.3 | 0.05–0.25 |
| Active Ingr. | 0.05 mg–25 mg | 1.0 mg–15.0 mg | which ingredients have been formulated in the manner described above. The method of practicing the present invention, and the slower dissolution rate achieved by replacing sugar with Palatinit in the hard confection, are illustrated by the following examples.

EXAMPLE I

The purpose of the experiment described in this example was to determine whether the use of Palatinit as a functional replacement for sugar and corn syrup in hard confections results in a longer dissolution time. The active ingredients used in this study were:

Sucrose (commercial grade)
Palatinit (type N coarse material for hard candies)
Corn Syrup (42DE from ADM Sweeteners)
Sunnette (Acesulfame-K from Hoechst Celanese Corp.)
FD&C Red #40 (Warner-Jenkinson Co.)
Artificial Cherry Flavor (H-5345 from Haarmann & Reimer Corp.)

Hard candies (with sugar/corn syrup or Palatinit having the following formulations were prepared:

| Ingredients | % |
|---|---|
| SUGAR HARD CANDY FORMULATION | |
| Sucrose | 49.360 |
| 42DE Corn Syrup | 32.910 |
| Water | 16.622/15.642 |
| Citric Acid/Buffered Citric Acid* | 0.800/1.780 |
| FD & C Red #40 (5% Sol) | 0.078 |
| Artificial Cherry Fl. (H-5345) | 0.120 |
| Sunnette (Acesulfame-K) | 0.110 |
| | 100.000 |
| PALATINIT HARD CANDY FORMULATION | |
| Palatinit (type N) | 74.900 |
| Water | 23.992/23.012 |
| Citric Acid/Buffered Citric Acid* | 0.800/1.780 |
| FD & C Red #40 (5% Sol) | 0.078 |
| Artificial Cherry Fl. (H-5345) | 0.120 |
| Sunnette (Acesulfame-K) | 0.110 |
| | 100.000 |

*45% Citric acid
15% sodium citrate
40% water

PREPARATION

The sugar candies were prepared by adding the 42DE corn syrup to a stainless steel pan followed by the addition of water. This mixture was heated and mixed to dissolve the corn syrup in water whereupon the sucrose was added with heating up to 300° F. The sugar mixture was cooled to 290° F. and citric acid (buffered or unbuffered) was added followed by the addition of Sunnette, color and flavor. The 60% buffered citric acid solution was prepared by heating 150 g citric acid, 50 g sodium citrate, and 133.3 g D.I. water. This formulation was molded at either 280° F. or 260° F. to form hard candies.

The Palatinit containing candies were prepared by adding water to the stainless steel pan along with Palatinit (type N). The mixture was heated to dissolve the Palatinit and then boiled at temperatures to 320° F. The Palatinit containing mixture was cooled to 290° F. and citric acid (buffered or unbuffered) was added, followed by the addition of Sunnette, color and flavor and molded at either 280° F. or 260° F. into the form of hard candies.

All candies were placed into glass jars with lids tightly secured. The candies were held for 24 hours or 48 hours before dissolution tests were conducted.

DISSOLUTION TEST

A disintegration tester was used to determine the dissolution rate of the candies prepared as described above. After weighing, the candies were placed into the tubes of the tester's basket which was placed into a 1 liter beaker with 800 ml of buffered saline solution at 37.5° C. The buffered saline solution contained 308 ml of 0.1 M citric acid, 692 ml 0.2 M dibasic sodium phosphate, 1.17 g NaCl and approximately 1 liter D.I. water to provide a 2 liter quantity. The pH of the buffered saline solution was approximately 6.7 to simulate the pH of saliva; the NaCl was used to simulate its salinity.

The candies used for the dissolution test weighed approximately 3.5 g each. There were 3 determinations consisting of a total of 18 replications which were averaged out to give the mean dissolution time in minutes.

RESULTS AND DISCUSSION

A factorial experiment was designed in which analysis of 16 runs were used to estimate the effects of acid type (citric acid or buffered citric acid), molding temperature (260 or 280° F.), and age prior to measurement time on the dissolution rate of the hard candies being tested which contained either sugar/corn syrup or Palatinit. In the design of this experiment, a particular treatment (independent variable) is referred to as a factor. This factorial experiment had four key factors affecting dissolution rate. They are:

(a) dissolution measurement time (24 and 48 hours).
(b) molding temperature 260 and 280° F.),
(c) acid type (citric acid and buffered citric acid), and
(d) sucrose or Palatinit.

Table 1 shows the factorial design and the results of the dissolution times (minutes) for each run; Table 2 shows the effects and interactions.

TABLE I

| Run | A Hr | B F. | C Acid | D | Dissolution Time (Min) |
|---|---|---|---|---|---|
| 1 | 24 | 260 | citric | sugar | 14.260 |
| 2 | 48 | 260 | citric | sugar | 14.140 |
| 3 | 24 | 280 | citric | sugar | 14.570 |
| 4 | 48 | 280 | citric | sugar | 14.950 |
| 5 | 24 | 260 | BCA | sugar | 14.320 |
| 6 | 48 | 260 | BCA | sugar | 14.020 |
| 7 | 24 | 280 | BCA | sugar | 14.710 |
| 8 | 48 | 280 | BCA | sugar | 14.840 |
| 9 | 24 | 260 | citric | PAL | 14.470 |
| 10 | 48 | 260 | citric | PAL | 15.950 |
| 11 | 24 | 280 | citric | PAL | 15.780 |
| 12 | 48 | 280 | citric | PAL | 15.780 |

TABLE I-continued

| Run | A Hr | B F. | C Acid | D | Dissolution Time (Min) |
|---|---|---|---|---|---|
| 13 | 24 | 260 | BCA | PAL | 15.810 |
| 14 | 48 | 260 | BCA | PAL | 15.910 |
| 15 | 24 | 280 | BCA | PAL | 15.550 |
| 16 | 48 | 280 | BCA | PAL | 16.110 |

Design Characteristics:
A-Dissolution in measurement time (24 hr or 48 hr)
B-Mold temperature (260° F. or 280° F.)
C-Acid type (citric acid or buffered citric acid (BCA))
D-Sugar or Palatinit (PAL)

TABLE II

| ESTIMATED EFFECT POSTERIOR PROBABILITY | | |
|---|---|---|
| A:Measurement time | 0.154 | 0.062 |
| B:Mold temperature | 0.301 | 0.391 |
| C:Acid type | 0.046 | 0.026 |
| D:Sugar or Palatinit | 1.319 | 1.000 |
| AB | 0.114 | 0.040 |
| AC | −0.031 | 0.025 |
| AD | 0.131 | 0.047 |
| BC | −0.014 | 0.025 |
| BD | −0.281 | 0.326 |
| CD | 0.054 | 0.027 |

From these tables it can be determined that sugar/corn syrup or Palatinit (D) had the greatest effect on dissolution rate, followed by molding temperature (B) then by molding temperature and sugar/corn syrup or Palatinit BD). A Bayes plot based on these data demonstrated that the sugar type had the greatest effect on dissolution rates. The molding temperature appeared to increase the dissolution time of sugar/corn syrup candies with a mean dissolution time of 14.2 minutes at 260° F. and 14.8 minutes at 280° F. The molding temperatures did not appear to have an effect with Palatinit candies since the mean dissolution time at 260° F. and 280° F. was 15.8 minutes.

At a molding temperature of 260° F., the Palatinit candies took 1.6 minutes (11.3%) longer to dissolve than sugar candies whereas, at a molding temperature of 280° F. they took 1.0 minute (6.8%) longer to dissolve than the sugar/corn syrup candies.

Example II

A Palatinit containing lozenge is prepared by adding water and Palatinit to a pan followed by heating to dissolve the Palatinit and boiling this mixture at temperatures to 320° F. This is followed by adding to the solution citric acid, dextromethorphan hydrobromide, artificial cherry flavor (H-5345), Sunnette (Acesulfame-K) and FD&C Red #40 (5% sol.) to provide a composition comprising on a % weight basis):

| Ingredient | % |
|---|---|
| Palatinit (type N) | 74.900 |
| Water | 23.706 |
| Citric Acid | 0.800 |
| Dextromethorphan hydrobromide | 0.286* |
| Artificial cherry flavor (H-5345) | 0.120 |
| Sunnette (Acesulfame-K) | 0.110 |
| FC & D Red #40 (5% sol.) | 0.078 |
| | 100.000 |

*10.01 mg for a 3.5 g lozenge

This material is molded at 260° F. into the form of a lozenge which is found to dissolve more slowly than similar lozenges containing sucrose/corn syrup thereby providing a slower and more sustained release of the dextromethorphan.

What is claimed is:

1. A hard, slowly dissolving, acidulated, amorphorus, boiled and molded lozenge confection essentially free of sugar and corn syrup which provides a slow, sustained release treatment of sore throats, coughs or nasal congestion comprising isomaltulose and an effective unit dosage amount of an antitussive, decongestant, antihistamine, or expectorant ingredient which is effectively released by sucking the lozenge during said period of slow sustained release.

2. The confection of claim 1 which contains a flavoring agent and another artificial sweetener.

3. The confection of claim 1 wherein the active ingredient is dextromethorphan, hexylresorcinol/menthol, phenylpropanolamine, dyclonine, menthol eucalyptus, benzocaine or cetylpyridinium.

4. The composition of claim 2 which contains an organic acid.

5. The composition of claim 4 wherein the organic acid is citric, malic, fumaric, succinic, adipic or tartaric acid.

6. The composition of claim 4 wherein hydrogenated isomaltulose is present in an amount of from 10 to 99 weight percent, the flavoring agent comprises from 0.01 to 2.5 weight percent, the artificial sweetener from 0.05 to 0.25 weight percent and the organic acid from 0.1 to 5.0 weight percent and the active ingredient is present in an amount of from 1.0 to 15 mg per unit dosage.

7. The composition of claim 6 which comprises from 50 to 98 weight percent hydrogenated isomaltulose, from 0.05 to 0.3 percent flavoring agent, from 0.05 to 0.25 percent artificial sweetener, from 0.2 to 2.5 percent organic acid and the active ingredient is present in an amount of from 0.05 to 25.0 mg per unit dosage.

8. The composition of claim 1 which contains from 0.01 to 2.0 weight percent of a coloring agent.

9. The composition of claim 1 wherein the coloring agent is Blue #1, Red #40, Yellow #5 or #6, beet, grape skin extract, carmel or a blend thereof.

10. The confection of claim 3 wherein the active ingredient is dextromethorphan hydrobromide in an amount of from 1.0 to 15.0 mg.

* * * * *

UNITED STATES PATENT AND TRADEMARK OFFICE
CERTIFICATE OF CORRECTION

PATENT NO. : 4,971,798

DATED : November 20, 1990

INVENTOR(S) : Kenneth A. Coia and Michael J. Lynch

It is certified that error appears in the above-identified patent and that said Letters Patent is hereby corrected as shown below:

At Column 2, line 62; change "lake" to ---lakes---.

At Column 6, line 55; insert ---titanium dioxide, carmine, annatto, beta carotene--- between "#6" and "beet".

On the title page, and in column 1, lines 3 and 4:
  In the title, insert --A-- between "AND" and "MEDICINALLY".

Signed and Sealed this

Nineteenth Day of May, 1992

Attest:

DOUGLAS B. COMER

*Attesting Officer*        *Acting Commissioner of Patents and Trademarks*

UNITED STATES PATENT AND TRADEMARK OFFICE
CERTIFICATE OF CORRECTION

PATENT NO.  : 4,971,798
DATED       : November 20, 1990
INVENTOR(S) : COIA et al.

It is certified that error appears in the above-indentified patent and that said Letters Patent is hereby corrected as shown below:

Claim 1, line 5: before "isomaltulose" insert
--hydrogenated--.

Signed and Sealed this

Seventeenth Day of June, 1997

Attest:

BRUCE LEHMAN

Attesting Officer

Commissioner of Patents and Trademarks